US006251103B1

(12) United States Patent
Berlin

(10) Patent No.: US 6,251,103 B1
(45) Date of Patent: Jun. 26, 2001

(54) PHOTOABLATIVE LASER EYE-TREATMENT METHOD

(76) Inventor: Michael S. Berlin, 8733 Beverly Blvd., Suite 301, Los Angeles, CA (US) 90048

( * ) Notice: Subject to any disclaimer, the term of this patent is extended or adjusted under 35 U.S.C. 154(b) by 0 days.

(21) Appl. No.: 08/237,221

(22) Filed: May 2, 1994

Related U.S. Application Data

(63) Continuation of application No. 07/642,700, filed on Jan. 16, 1991, which is a continuation of application No. 07/389,170, filed on Aug. 3, 1989, which is a division of application No. 07/054,282, filed on May 26, 1987, now Pat. No. 4,846,172.

(51) Int. Cl.$^7$ ..................................................... A61M 5/06
(52) U.S. Cl. .................................. 606/15; 606/3; 606/10; 606/17
(58) Field of Search .......................... 606/2–4, 7, 10–17; 128/897, 898; 607/88–93

(56) References Cited

U.S. PATENT DOCUMENTS

| | | | |
|---|---|---|---|
| 3,982,541 | * 9/1976 | L'Esperance, Jr. | 128/395 |
| 4,461,295 | * 7/1984 | Herrick | 606/4 |
| 4,470,407 | * 9/1984 | Hussein | 606/7 |
| 4,538,608 | * 9/1985 | L'Esperance, Jr. | 606/6 |
| 4,559,942 | * 12/1985 | Eisenberg | 606/6 |
| 4,583,539 | * 4/1986 | Karlein et al. | 128/395 |
| 4,658,816 | * 4/1987 | Ector, Jr. | 128/397 |
| 4,660,546 | * 4/1987 | Herrick et al. | 128/898 |
| 4,791,927 | * 12/1988 | Menger | 606/3 |

OTHER PUBLICATIONS

"Excimer Laser Photoablation in Glaucoma Filtering Surgery" by Berlin et al; Am. J. Ophthal. vol. 103, No. 5, 1987, pp. 713–714.*
"Laser Surgery: $CO_2$ or HF" by Wolbarsht IEEE J of Quant. Electronics; vol. QE–20; No. 12 Dec. 1984 pp. 1427–1432.*
"Ophthalmic Lasers : Photocoagulation Photoradiation and Surgery" by L'Esperance ; The C. V. Mosby Company St Louis 1983 pp. 529–538 & 554.*

* cited by examiner

Primary Examiner—David M. Shay
(74) Attorney, Agent, or Firm—Banner & Witcoff, Ltd.

(57) ABSTRACT

Transocular and periocular laser delivery system for treatment of eye diseases wherein a fiberoptic element is passed through a perforation made either by paracentesis of eyeball encapsulating tissue (i.e.—cornea, sclera) or by the fiberoptic element itself so that the fiber actually penetrates into a chamber therein. The penetrating fiber end is then juxtaposed to the tissue to be treated while the external fiberoptic end is coupled either to an excimer laser emitting ultraviolet radiation (in the range of 193 to 351 nanometers) or to certain lasers emitting infrared radiation, the radiated pulses therefrom being directed through the transocularly-positioned fiber to be absorbed by chromophores in the target tissue (cataractous lens, trabecular meshwork, vitreous membranes, tear duct occlusion) where removal by photoablation is effected. Photoablation by way of the fiberoptic element creates a portal for filtration of aqueous fluid in the case of glaucoma or allows removal of cataractous lens tissue, vitreous hemorrhage or membranes or other tissue occluding tear duct passages in a manner promoting controlled healing, minimizing inflammation and scarring.

8 Claims, 2 Drawing Sheets

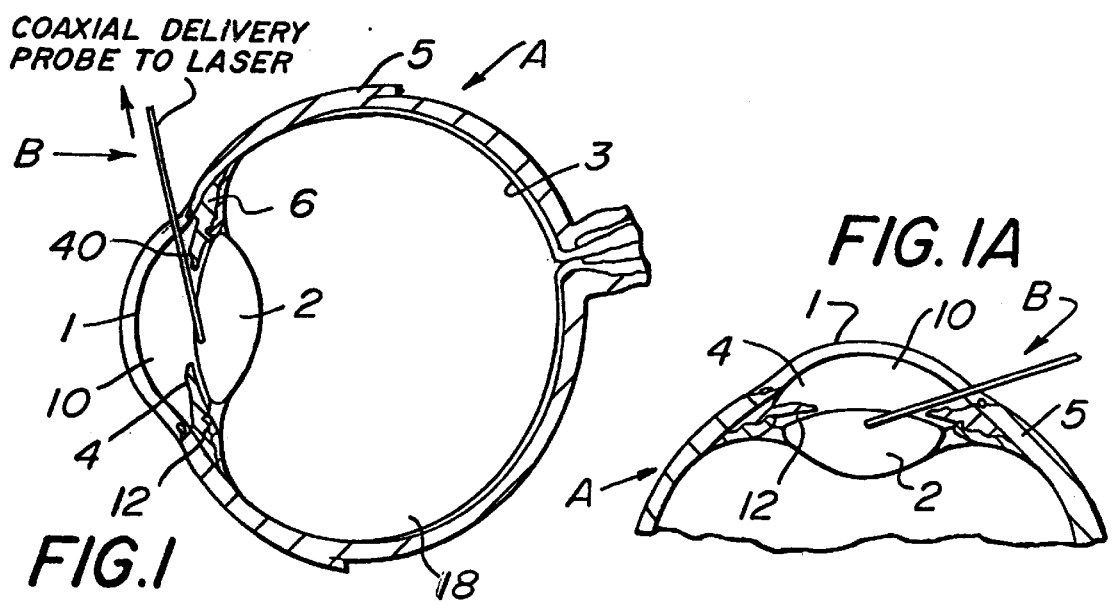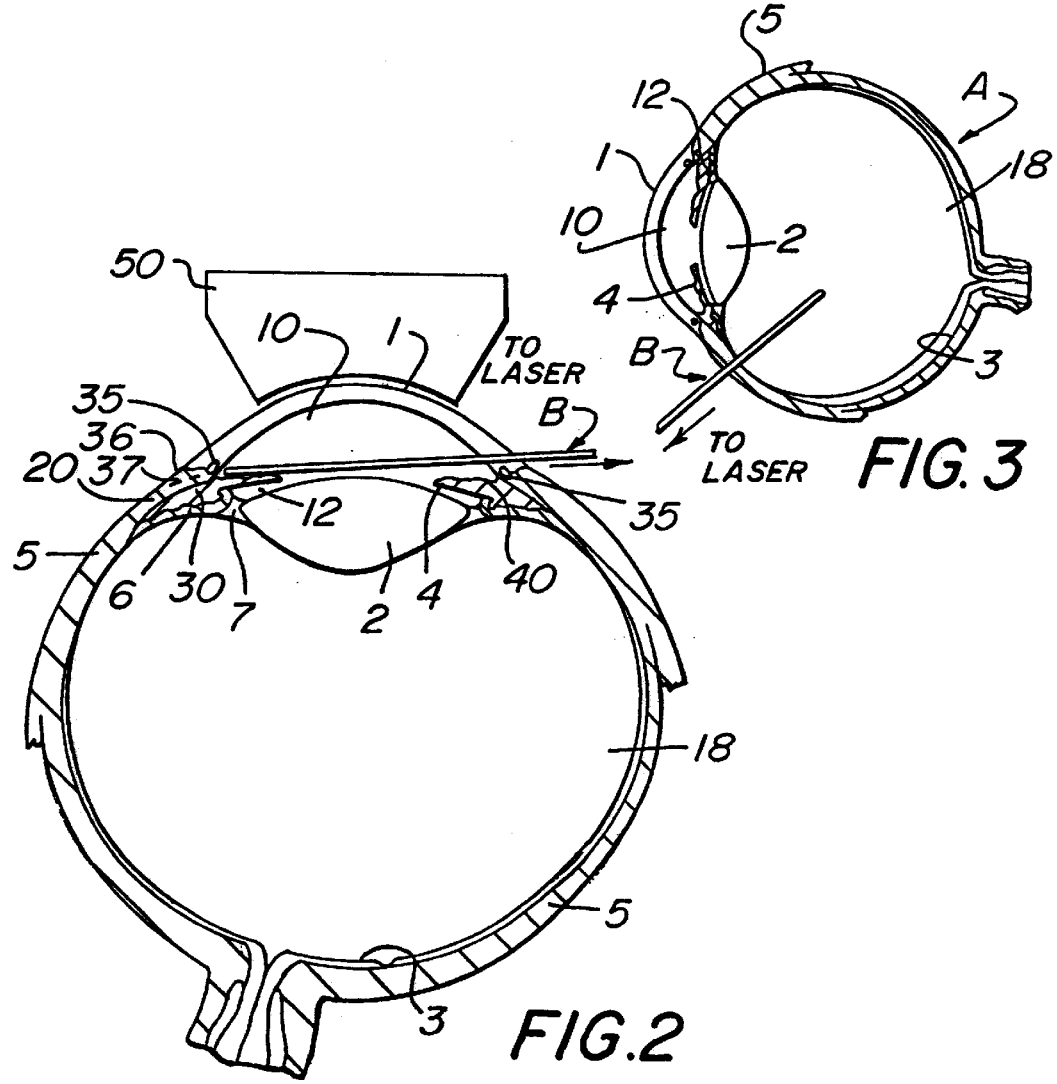

PHOTOABLATIVE LASER EYE-TREATMENT METHOD

This is a continuation of application Ser. No. 07/642,700, filed on Jan. 16, 1991, which is a continuation of Ser. No. 07/389,170, filed on Aug. 3, 1989 of Michael S. Berlin for PHOTOABLATIVE LASER EYE-TREATMENT METHOD which is a division of Ser. No. 07/054,282 filed May 26, 1987, now U.S. Pat. No. 4,846,172.

BACKGROUND OF THE INVENTION (1) Field of the Invention

This invention relates to the application and delivery of laser energy to ocular tissue for controlled removal of various components thereof. More particularly, this invention pertains to surgical apparatus and procedures involving ultraviolet excimer lasers or infrared lasers in combination with fiberoptic elements for effecting photoablation of ocular and periocular tissue, especially in connection with cataract removal or treatment of eye diseases, such as glaucoma, vitreous humor abnormalities or tear duct ostructions. The main thrust of this invention concerns the coupling of ultraviolet excimer or infrared lasers to fiberoptic elements which have been passed through perforations in eyeball encapsulating and periocular tissue—for example, the cornea or sclera, after paracentesis thereof—and then advanced transocularly so that the penetrating end is juxtaposed adjacent the diseased tissue (cataractous lens, trabecular meshwork or angle structures, vitreous membranes, occluded tear duct passages or the like), whereby the coherent (UV or infrared) radiation is delivered through the fiber and the emission therefrom is directed immediately and precisely upon the target sites.

(2) Prior Art (a) Cataract Removal

Cataract is a disease of the eye in which the crystalline lens or its capsule becomes opaque or clouded. Current techniques for removing cataractous tissue require incisions in the cornea large enough to physically withdraw the lens, which can measure upwards of 10 mm., or the use of ultrasound generating devices to pulverize the lens in situ. The latter instance, in which a corneal incision of at least 3 mm. is required, imposes a potential risk of damage to adjacent intraocular structures as a result of dispersement of ultrasonic energy within the eye's fluid medium and/or from the free floating lens particles created during the fragmentation process. Both of these latter procedures require the use of suture materials to close the corneal wounds created to allow access to the interior of the eye.

With the development of intraocular lenses capable of being inserted through small surgical wound apertures, it has become possible to manipulate through a wound small enough to be self-sealing, making suture closure no longer mandatory. By avoiding the need for large iatrogenic wounds and the necessity of sutures, healing becomes more rapid and the risks of surgically induced astigmatism are reduced as are the recovery and rehabilitation periods.

Accordingly, it is desirable to remove the lens tissue itself in such a way as to minimize corneal incision size and in a manner least disruptive to the neighboring tissue, thereby delimiting any induced inflammatory response and its sequelae.

(b) Glaucoma surgery

Glaucoma refers to a series of relatively common eye disorders in which pressure within the eye is sufficiently high as to result in damage to sensitive intraocular structures, including the retina and optic nerve. Glaucomas are classified as primary (including chronic open angle glaucoma, angle closure glaucoma, mixed mechanism glaucoma and infantile glaucoma) and secondary (related to other diseases of the eye). The elevation of intraocular pressure ultimately leads to irreversible destruction of the optic nerve. The clinical symptoms, which are not readily recognized in the early stages, are characterized mainly by a slow, relentless, progressive narrowing of the field of vision, and decrement in visual integration processing, including diminished dark adaptation. In the absence of treatment, the eventual outcome is total loss of vision together with severe eye pain.

Present surgical techniques to lover intraocular pressure (recruited when medication has proven inadequate to decrease fluid flow into the eye or to increase fluid outflow) include procedures enabling fluid to drain from within the eye to extraocular sites. However, these drainage or "filtering" procedures, as they are called, not only induce risk to the lens causing cataract, but often fail by virtue of their closure resulting from the healing of the very wound created for gaining access to the surgical site. In creating the egress by photoablation, less inflammation at the egress site is induced than by current techniques, thus prolonging filtration wound function.

(c) Vitreous Humor

The vitreous humor is that transparent portion of the eye between the lens/zonule diaphragm and the retina. It is attached to the retina and composed of a network of fibrils which, if stressed, can induce the retina to detach or wrinkle with subsequent loss of vision.

Treatment of diseases of the vitreous humor, including hemorrhage, membranes and foreign bodies, requires cutting devices which remove the diseased portions without stressing the attached fibrils to avoid retinal detachment. Current devices include mechanical micro-scissors and guillotine suction cutters, all of which produce vibration shocks in their actions. The advantage of applying photoablation to these tasks is the ability to remove this diseased tissue with less disruption of the local environs together with improved surgical control. Intra-vitreal photoablation is now possible with this fiberoptic device.

(d) Periocular Surgery

The lacrimal drainage system carries tears from the eye to the nasopharnx. Obstruction can occur from the eyelid punctum to the nasolacrimal duct.

Therapies currently employed include dilation approaches which often reclose and dacryocystorhinostomy in which a surgical window in created by removing bone and mucosa from an incision at the side of the nose. However, using photoablation, with a cannula under direct visualization, a flexible fiberoptic catheter is passed through the punctum to the site of the obstruction followed by the application of laser energy. Thus, photoablative removal of the obstruction precludes the necessity for surgical incision for bone removal, thereby greatly decreasing the morbidity and healing time.

(e) Laser Technology

Lasers were first used in 1965 to repair retinal detachment. The procedure involved chorioretinal coagulation in which a laser beam positioned from without the eye was used to achieve fusion of the retina and the choroid. See, for example U.S. Pat. No. 3,720,213 to Hobart et al, and U.S. Pat. No. 3,703,176 to Vassiliadas et al, wherein the techniques consisted of introducing a laser beam from outside the cornea, and by employing the refractive media of the eye itself, the laser radiation was directed in such a manner that it was concentrated at a selected point upon the retina/choroid so that the tissues in a very localized area were congealed.

In U.S. Pat. No. 4,207,894 to Choy and U.S. Pat. No. 4,469,098 to Davi are shown laser systems for performing coronary angioplasty and the like wherein a flexible fiberoptic probe is actually inserted into and through body tissue to impinge directly at the pathological site. However, both of these systems utilize high powered $CO_2$ or Nd YAG lasers in which large amount of heat is generated to perform thermal excisions or to thermal vaporization of the tissue lattice.

U.S. Pat. No. 4,538,608 to Esperance shove a method and apparatus for removing cataractous lens tissue in the eye by either Neodymium-YAG (infrared-thermal) or excimer (ultraviolet) laser radiation, the laser beam again being introduced from without the eye and applied afocally or diffusely as it enters the eye through the cornea. Meyers U.S. Pat. No. 4,601,288 employs another externally introduced YAG laser device for focussing multiple laser pulses from a position outside the eye and passing the beam through the cornea to a point at the back surface of the lens in order to effect removal thereof.

U.S. Pat. No. 4,391,275 to Fankhauser et al and U.S. Pat. No. 4,558,698 to O'Dell relate to methods for surgical treatment of glaucoma by directing a YAG (Yttrium-Aluminum-Garnet) laser from outside the eye such that the laser beam passes through the cornea to focus upon the trabecular meshwork in the region of the irido-corneal angle. Reestablishment of the free circulation of the aqueous humor is enabled by laser perforation of the wall separating the anterior chamber of the eye from the canal of Schlemm on the level of the trabecular meshwork, or by opening the supra-choroidal space, or by perforating the iris.

In contrast to thermal energy produced by the infrared lasers, such as the Nd-YAG systems, the high photon energies of ultraviolet light can directly break chemical and biologic bonds without interacting with the material in question, namely eye tissue, in a manner as would cause temperature elevation. By photoablation, both ultraviolet and infrared radiation can be used to drastically alter the chemical behavior of a system in a "cold" environment. This becomes significant for controlled removal of organic substances, such as living tissue, in contradistinction to treatments in which heat is generated, e.g by thermal infrared lasers, which could damage, if not destroy, delicate eye tissue adjacent to the target sites to be removed. A problem associated with the use of ultraviolet radiation is that its emission could potentially injure the retina, or induce changes in DNA. Because UV radiation may be dispersed or conducted into surrounding portions of the eye without the use of fiber control, such UV treatment presented unacceptable risk in the past.

Excimer lasers form a group of pulsed high pressure gas lasers which emit at 193 nanometers ($ArF^e$), 248 nm ($KrF^e$), 308 nm ($XeCl^e$) and 351 nm ($XeF^e$) in the ultra-violet spectrum. In contrast to the thermal infrared radiation from some Nd-YAG or $cO_2$ lasers or the like, the high energy UV photons from excimer lasers at photoablative fluence levels interact with the absorber molecules, leading to chemical bond breaking, ionization or electronic excitation. The present invention deals with the delivery of photoablative fluence levels of ultraviolet and infrared photons to the precise point of the target tissue of the eye by fiberoptic delivery systems without impinging upon the overlying or surrounding tissue or upon the tissue at the point of entry into the eye by the beam itself.

SUMMARY OF THE INVENTION

The present invention is directed to the application and delivery of laser energy through the eye by passing laser radiation, including ultraviolet and infrared, through a fiberoptic element which has been inserted through a perforation in the eye and thence juxtaposed with respect to the tissue where the laser emission is targeted, thereby effecting photoablative removal of such target tissue.

In cataract removal by the instant invention, laser energy is applied to the lens through a fiberoptic delivery system probe perforating the eye through a previously made limbal incision and then transocularly by way of the anterior chamber into immediate adjacency with the lens. The ablative products of the photodecomposition of the lens are evacuated concurrently with controlled irrigation and the internal laser application to the lens itself. In this form of intracapsular cataract surgery, portions of the lens capsule are retained, thereby maintaining intraocular pressure as well as transparency of the fluid media.

In connection with glaucoma treatment, laser energy is applied by way of a fiberoptic element introduced through a surgically performed opening in the cornea or sclera, after which the fiber is transocularly advanced through the anterior chamber to a position within the irido-corneal angle adjacent the trabecular meshwork. The photoablative radiation directed through the fiberoptic element is emitted at the angle structures to create a fluid passageway between the anterior chamber of the eye and the potential supra-scleral/sub-Tenon's space (or alternatively, into or through the Canal of Schlemm), creating a filtering bleb and thereby relieving intraocular pressure. Surgical trauma to the overlying conjunctival and Tenon's tissue, both extremely subject to scarring, is thereby minimized.

As in cataract surgery, the technique is performed by means of a fiberoptic delivery system piercing the eye-encapsulating tissue. Tissue products generated by laser photoablation may be evacuated concurrently therewith, and intraocular pressure as well as transparency may be maintained via infusion. Prior glaucoma procedures resulted in an extremely high frequency of failures because of the healing of the very wound created to gain access to the surgical site via the incising conjunctiva and Tenon's capsule. By creating an aqueous humor egress route which avoids initial trauma to the external site of filtration, the present invention enables a significantly greater opportunity for success, including the ability to titrate the amount of photoablative surgery necessary to result in a measured lowering of intraocular pressure, relatively risk-free operation and a "small incision" technique (±400 micron diameter), such that the procedure may be performed on an outpatient basis to avoid the costs and discomforts attendant to hospitalization.

In connection with vitreous surgery, photoablative laser energy is again applied by way of a fiberoptic delivery system transocularly advanced to a position inside the vitreous cavity for the purpose of excising all or parts of abnormal tissue (i.e. scar, blood or foreign bodies). Again, evacuation, irrigation and intraocular pressure maintenance systems function simultaneously, as required.

It in therefore an object of this invention to provide a surgical procedure for controlled removal of various ocular tissue with homeostatic maintenance, greater patient safety and minimized surgically induced refractive change, thereby minimally altering the function of the eye while preserving or restoring vision.

Another object of this invention is to provide a fiberoptic laser delivery system for intraocular eye surgery which will enable surgical procedures to be employed through smaller incisions, allow for more rapid healing in the case of cataract removal, yield less scar Induction in the case of glaucoma therapy, and permit improved control of homeostasis during vitrectomies, lensectomies and trabeculectomies.

Still another object of this invention is to provide a fiberoptic delivery system for laser surgery in the eye wherein thermal and/or radiation damage to the eye is minimized, irradiated target tissue is fragmented into small volatile and easily ejectable components, and wherein a filtering wound is produced which will more likely remain patent.

Other objects of this invention are to provide an improved method which is easily and economically performed, and highly efficient and effective in operation.

BRIEF DESCRIPTION OF THE DRAWINGS

With the above and related objects in view, this invention consists of the details of construction and combination of parts as will be more fully understood from the following detailed description when read in conjunction with the accompanying drawing in which:

FIG. 1 is a simplified side cross-sectional view of the eye showing the application of the present invention to the performance of cataract surgery.

FIG. 1A is a fragmentary top sectional view thereof.

FIG. 2 is a simplified side sectional view of the eye showing the application of the present invention to the performance of glaucoma surgery.

FIG. 3 is a simplified side sectional view of the eye showing the application of the present invention in connection with a vitrectomy.

DETAILED DESCRIPTION

Figure 4:
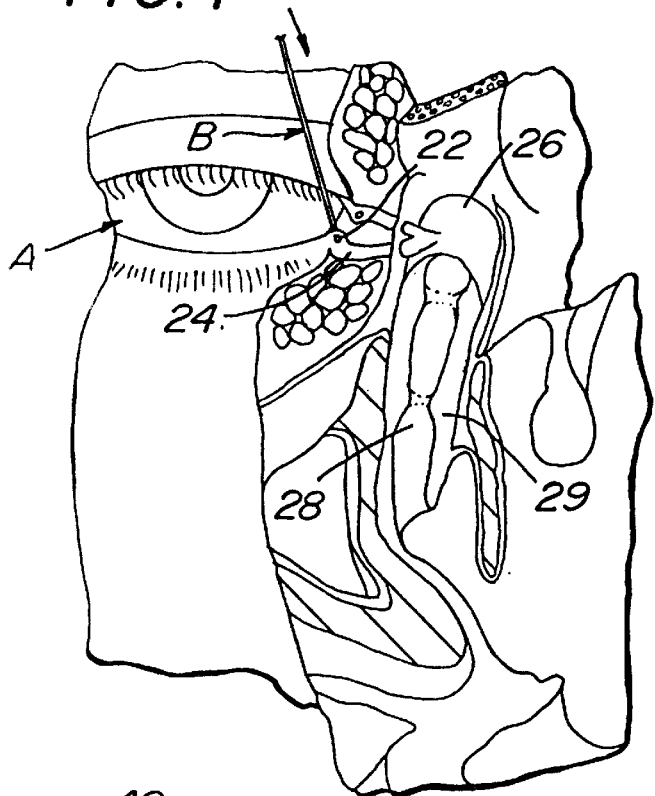
FIG. 4 is a fragmentary front elevational view of the eye portion of the face, partially broken away to show the application of the present invention to removal of occlusions in the tear ducts.

Referring now in greater detail to the drawings in which similar reference characters refer to similar parts, I show an apparatus and method for the surgical treatment of the eye, generally designated as A, by means of a laser coupled to a transocular probe B in the form of a coaxial fiberoptic element. The coaxial fiberoptic element B is passed through a perforation in an outer encapsulating tissue of the eye (i.e.—cornea, sclera) previously made by a sharp pointed blade or other instrument (not shown) under the direct visual control of the ophthalmologist. The penetrating end of the probe B is passed through an eye chamber or tear duct passage, for example, the anterior chamber, the vitreous cavity or the like, into juxtaposition with the target tissue. The laser device which is coupled to the exterior end of the fiberoptic element is then activated to deliver photoablative fluence ultraviolet or infrared pulses through the fiberoptic probe so that the emerging beam is at energies which are at or above the photoablative threshold for the target tissue chromophores, after which the emitted beam exiting from the fiber is directly and critically targeted on the tissue to be removed. As the emitted radiation impinges upon the target tissue, the probe B is slowly advanced whereby the target tissue is ablatively photodecomposed.

The eyeball A includes the cornea 1 which allows the transmission of light beams through the eye's crystalline lens 2 to the retina 3. The iris 4 controls the pupillary opening. The cornea 1 and the sclera 5 define the outer layers of the eye. The lens 2 is supported by ciliary body 6 via zonules 7. The irido-corneal angle 40 is defined by the space between the iris 4 and the cornea 1, within the recess of which lies the trabecular meshwork. The ciliary body 6 along with the iris 4 defines the boundary between the anterior chamber 10 and the posterior chamber 12 both containing the aqueous humor produced by the ciliary processes and draining at the trabecular meshwork between the lens 2 and the iris 4.

The mode and method of the present invention for performing a lensectomy on a cataractous lens is best illustrated in FIGS. 1 and 1A. Following local anesthesia, the surgeon makes a small incision at the margin of the cornea 1 or sclera 5 with a sharp-pointed surgical blade. The fiberoptic coaxial probe B is then inserted through the perforation in the cornea 1 and passed through the anterior chamber 10 to a position where the end thereof is immediately adjacent the portion of the lens 2 on which the laser beam is to be impinged. The external end of the fiberoptic element B is coupled to a laser device, such as an ultraviolet excimer laser, for example $XeCl^e$, (or an infrared laser, for example Raman-shifted Nd-YAG or Erbium YAG), to emit radiation with above ablative threshold fluence through the fiberoptic delivery system. The depth of ablation at the lens for each excimer pulse is calculated beforehand, and the fiber-optic probe is slowly advanced following microcapsulectomy photoablation whereby photo-decomposition of the cataractous tissue is continued until the desired portions of the lens 2 (i.e. capsule, nucleus, cortex) are removed by photoablation and evacuation. The photochemical effects of the laser on the lens tissue result in ablative decomposition in which the irradiated tissue is reduced to small volatile fragments which are withdrawn by conventional techniques through the probe via the aperture wounds originally created in the cornea 1. Intraocular pressure is maintained during photoablation as well as transparency of the fluid media by way of aspiration/infusion through the coaxial probe element B. The specific manner of coupling the laser is not part of the present invention, but reference may be made to U.S. Pat. No. 4,469,098 or to U.S. Pat. No. 4,537,193 for appropriate mechanisms to interface the same.

In FIG. 2, there is illustrated the technique of the present invention as applied to the treatment of glaucoma by way of a procedure known as a trabeculectomy ab interno. In this procedure, again performed under an operating microscope and following local anesthesia, a tiny paracentesis opening (which is self-sealing) is made in the peripheral cornea 1 or sclera 5 adjacent the limbus by means of a sharp-pointed blade in a direction toward the internal apex of the irido-corneal angle 40. The anterior chamber depth is maintained by the aspiration/infusion probe device B and/or by sodium hyaluronate (Healon) following the paracentesis opposite the proposed filter site. The flexible fiberoptic element B, mounted on the end of a handpiece containing or connected to a laser (not shown) capable of emitting a photoablative beam, is guided through the surgically-made paracentesis hole and advanced transocularly through the anterior chamber 10 toward the irido-corneal angle 40. Using a goniolens 50, or under other visual microscopic control, the end of the fiberoptic probe B is juxtaposed at or about the trabecular meshwork 30 whereupon the photoablative ultraviolet or infrared emission is caused to effect a photoablative opening through the trabecular meshwork 30, Schlemm's canal 35 or angle sclera. With slow advancement of the fiber probe B through the sclera and into the episcleral space 36 such that the aqueous humor gains access to the sub-Tenon's capsule 37, introcular pressure becomes relieved. Initial evaluations on human eye bank models reveal thresholds for perforation at the angle 40 of about 80 to 100 pulses utilizing up to 40 millijoules/mm$^2$ and employing a wave length of 308 nm with a repetition rate of 20 Hz. Thus, the laser energy impinging directly at the target site re-establishes drainage between the anterior chamber 10 and the sub-Tenon's space 37 and possibly also the Canal of Schlemmm 35. Withdrawal of the fiber probe B permits Healon from the anterior chamber 10 to access the sub-Tenon space 37, dissecting a filtration bed and creating a bleb. The fiber B is then entirely removed and topical antibiotic/steroid drops instilled.

Advantages of the foregoing procedure in which the laser pulses are delivered intraocularly through the fiberoptic element B include a minimimum of trauma to overlying, potentially inflammatory tissue, easily titratable filtration volume and facile repetition in the event of failure or should additional filtration become necessary to control intraocular pressure. The use of photoablative lasers ab interno is more unlikely to evoke a fibrotic scar-inducing response than transcorneally projected visible or infrared thermal or Q-switched mechanically-disruptive lasers wherein tissue-laser interaction is thermal or mechanical in creating passages in the trabecular meshwork or sclera. Exposure of the tissue surrounding the target area is minimized by almost direct application of the laser energy to the target tissue itself via the fiberoptic element B and absorption of the products of ablation by the Healon.

In rabbit, usually a very poor model for glaucoma surgery, filtering blebs created by the techniques of the instant invention have continued to function as long as three months post-operatively with quiet anterior chambers and no detected corneal or lens abnormalities. Essentially what is seen post-operatively is a hole matching the fiber diameter with no perceptible change in the Tenon's or conjunctiva.

Referring now to FIG. 3, there is illustrated the techniques of the present invention for performing a vitrectomy wherein blood, abnormal tissue or foreign bodies in the vitreous humor of the posterior cavity 18 may be photoablatively decomposed by the photochemical action of the laser radiations delivered through the coaxial fiberoptic probe B. The cornea 1 or the sclera 5 at the pars plana is incised under microscopic control with a sharp-pointed surgical super blade after suitably anesthetizing the eye. The coaxial fiberoptic element B is then passed through the surgical incision, and the end thereof is directed immediately adjacent the foreign or abnormal tissue within the vitreous humor and/or the tissue is brought to the instrument via suction aspiration and infusion, at which time the photoablative ultraviolet or infrared emission is directed through the fiberoptic element and focussed directly upon the tissue to be ablated. During photo-decomposition of the abnormal tissue, products of the process are evacuated. Then, the fiberoptic probe B is withdrawn, the entrance site closed, and medications administered in a conventional manner. This procedure has been successfully performed on the eyes of rabbits as well as on human eye bank eyes.

Referring now to FIG. 4, there is shown the procedure of the instant invention for relieving obstructions in the various tear passages. With the cannula under direct visualization, the flexible fiberoptic probe B is passed through the punctum 22 to a position adjacent the potential sites of obstruction, for example, canaliculus 24, the lacrimal sac 26 or duct 28 next to the "valve" of Hasner 29. Energy from the laser is applied to the external end of the fiberoptic element, and the probe B is slowly advanced so as to effect photoablative vaporization of the tissue at the distal end thereof. This technique avoids the necessity for surgical incision of the face and mechanical bone removal, thereby diminishing healing time and decreasing morbidity. It is to be especially noted that the probe B does not pass through an eye chamber during periocular procedures of the instant invention, as was the case of transocular penetration of eye encapsulating tissue during photoablative lensectomy, trabeculectomy or vitrectomy, but the probe is passed between the outer surface of the eye and the membranes supporting the eye to a position immediately adjacent the afflicted channel involving tear duct obstruction. However, the same principle of directing the fiberoptic probe B to a position adjacent the site and directing the photoablative laser energy through the fiberoptic element to egress at the site of the pathological channel tissue applies.

Figure 5:
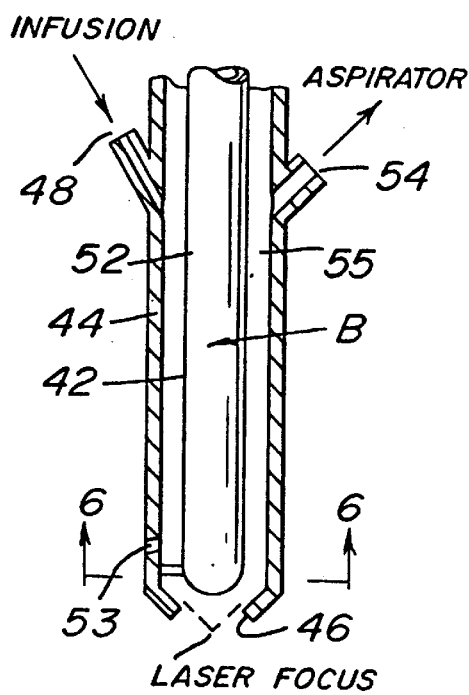
FIG. 5 is a side elevational view, and partly broken away, of one form of a fiberoptic delivery probe embodying this invention.
Figure 6:
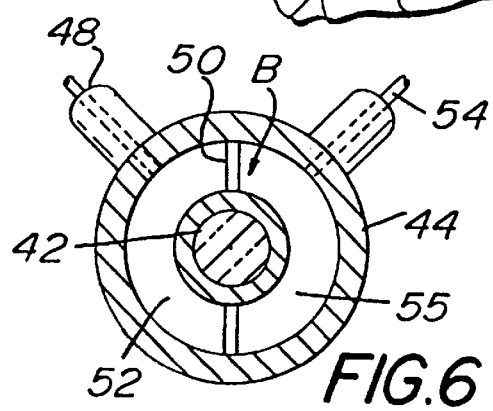
FIG. 6 is a sectional view taken along lines 6—6 of FIG. 5.

In FIGS. 5 and 6, there is shown an embodiment of the present invention in which the probe B comprises a fiber element 42 coaxially disposed within a catheter or cannula 44 having a symmetrically disposed axial port 46 at the tip end of the fiber element whose terminus is lenticular. Infusion of fluid media is directed through inlet port 48 into a jacketed space 52 defined between the fiber element 42, its concentric catheter 44 and internal web or spider 50, from where such fluid is syringed into the eye through one or more peripheral ports 53 at the distal end of the probe. Aspiration or suction means is applied to port 54 which communicates with annular jacket 55 on the other side of web 50 whereby fluid or debris may be drawn from the eye into axial port 46 for subsequent removal via the aspiration port 54.

Figure 8:
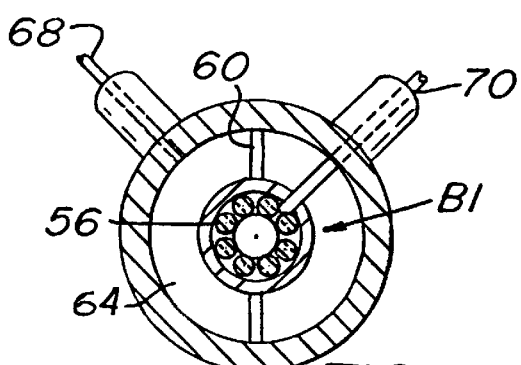
FIG. 8 is a sectional view taken along lines 8—8 of FIG. 7.
Figure 7:
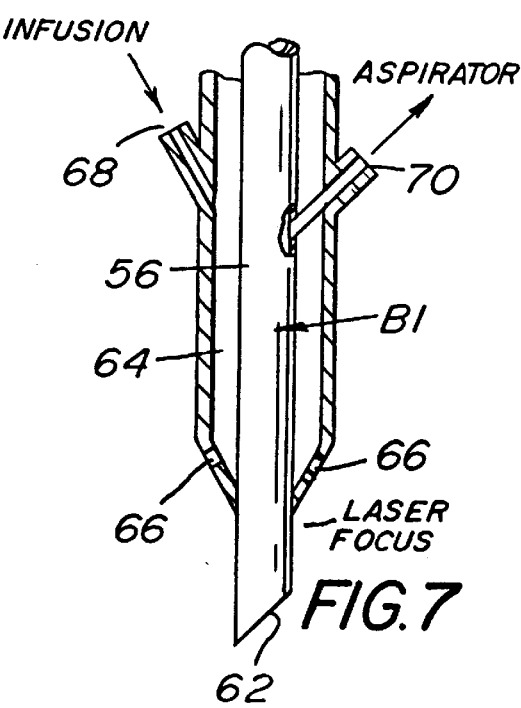
FIG. 7 is a side elevational view, and partly broken away, of another form of a fiberoptic delivery probe embodying this invention.

In FIGS. 7 and 8, I show another embodiment B1 of a probe whose fiber element 56 is hollow while being supported coaxially within its cannula 58 by suitable struts 60. The end of the fiberoptic element 56 protrudes beyond the distal end of the cannula jacket 58 which is tapered closed at the bottom of the annular space 64. An infusion port 68 communicates with the annular space 64 whereby fluid may be infused into the eye through discharge ports 66 peripherally disposed about the distal end of the cannula jacket 58. A suction port 70 communicates with the central bore of the fiberoptic element 56 to enable fluid and debris to be aspirated through the hollow tip 62 of the fiberoptic element 56 after laser radiation and/or infusion has been performed. The configuration of the fiber element 56 can be in the form of a hollow tube or as a bundle of individual fibers peripherally arranged about a central bore. The tip 62 of the fiberoptic element 56 may have a biased terminus with a skewed aperture to enable radiation emerging therefrom to exit at an angle to the longitudinal axis of said fiberoptic element where certain control is surgically required.

Photoablative decomposition can be performed with many wave lengths, including ultraviolet and infrared wave lengths dependent upon the target chromophore absorbers. The 308 nanometer (XeCl$^e$) excimer laser has proven extremely successful, the 193 nm wave length of the ArF$^e$ appears to provide even a safer wave length with 248 nm (KrF$^e$) and 351 nm (XeF$^e$) excimers efficaceous on experimental animals as well as eye bank eyes. Infrared laser radiations approximating 2.8 to 3.0 microns have also proven effective in all of the photoablative procedures set forth above.

Although this invention has been described in considerable detail, such desciption is intended as being illustrative rather than limiting, since the invention may be variously embodied without departing from the spirit thereof, and the scope of the invention is to be determined as claimed.

What is claimed is:

1. A method for surgical treatment of the tear ducts and passages of the eye containing occlusions which prevent the flow of tears comprising the steps of:
   (a) introducing a fiberoptic probe between the outer surfaces of the eye and supporting membranes therefor until the penetrating end of the probe is adjacent the punctum,
   (b) surgically entering the tear passages to localize obstruction to tear flow,
   (c) coupling the exterior end of said fiberoptic element to a photoablative laser selected from the group consisting of an ultraviolet excimer laser having a wavelength in the range of 193 nanometers to 351 nanometers and an infrared laser having a wavelength in the range of 2.8 to 3.0 microns, and emitting photoablative radiating laser pulses whereby the radiated photoablative laser pulses emitted at the distal end of the probe causes photodecomposition of occluding tissue in the tear ducts or passages, and
   (d) advancing the probe so as to effect cannulization of occlusive tissue and bone adjacent thereto by photoablation thereof and creating patentcy of said ducts and passages by re-establishment of tear flow to the nasopharynx.

2. The method of claim 1 wherein the wave length of the laser radiation is in the range of 2.8 to 3.0 microns.

3. The method of claim 1 wherein said ultraviolet excimer laser is a XeCl laser.

4. The method of claim 1 wherein said infrared laser is a selected from the group consisting of Raman shifted Nd:YAG and Erbium:YAG lasers.

5. The method of claim 1 wherein the wave length of the laser radiation is in the range of 193 nanometers to 351 nanometers.

6. The method of claim 5 wherein the wave length of the laser radiation is substantially 308 nanometers.

7. The method of claim 1 wherein the fiberoptic element is coaxially disposed within a supporting cannula.

8. The method of claim 7 wherein said supporting cannula includes an infusion port and an aspiration port in communication with corresponding spaces between the cannula and the fiberoptic element therein.

* * * * *